(12) United States Patent
Wu et al.

(10) Patent No.: US 8,355,529 B2
(45) Date of Patent: Jan. 15, 2013

(54) MOTION CAPTURE APPARATUS AND METHOD, AND MOTION CAPTURE PROGRAM

(75) Inventors: Weiguo Wu, Tokyo (JP); Keisuke Yamaoka, Tokyo (JP); Yuyu Liu, Tokyo (JP)

(73) Assignee: Sony Corporation, Tokyo (JP)

( * ) Notice: Subject to any disclaimer, the term of this patent is extended or adjusted under 35 U.S.C. 154(b) by 1519 days.

(21) Appl. No.: 11/764,407

(22) Filed: Jun. 18, 2007

(65) Prior Publication Data
US 2008/0112592 A1 May 15, 2008

(30) Foreign Application Priority Data

Jun. 19, 2006 (JP) .................................. 2006-169070

(51) Int. Cl.
G06K 9/00 (2006.01)
G06T 17/00 (2006.01)
H04N 7/18 (2006.01)
(52) U.S. Cl. .......................... 382/103; 345/420; 348/154
(58) Field of Classification Search .................. 382/103, 382/107, 236; 348/154, 155, 169, 170, 171, 348/172, 208.1, 208.2, 208.14, 208.16; 345/8, 345/156, 174, 181, 420
See application file for complete search history.

(56) References Cited

U.S. PATENT DOCUMENTS

| 6,269,172 B1 * | 7/2001 | Rehg et al. ..................... 382/103 |
| 6,295,367 B1 * | 9/2001 | Crabtree et al. ................ 382/103 |
| 6,324,296 B1 * | 11/2001 | McSheery et al. ............ 382/107 |
| 6,774,885 B1 | 8/2004 | Even-Zohar |
| 8,023,726 B2 * | 9/2011 | Sundaresan et al. .......... 382/154 |
| 2003/0122831 A1 | 7/2003 | Jeong |
| 2003/0138130 A1 | 7/2003 | Cohen |
| 2004/0119716 A1 | 6/2004 | Park |

FOREIGN PATENT DOCUMENTS

| EP | 1 335 322 | 8/2003 |
| JP | 2005-040556 | 2/2005 |
| WO | WO 00/17767 | 3/2000 |

(Continued)

OTHER PUBLICATIONS

D. Demirdjian et al. "Constraining Human Body Tracking", Proceedings of the International Conference on Computer Vision, vol. 2, pp. 1071-1078, 2003.

(Continued)

*Primary Examiner* — Abolfazl Tabatabai
(74) *Attorney, Agent, or Firm* — Finnegan, Henderson, Farabow, Garrett & Dunner, L.L.P.

(57) ABSTRACT

A motion capture apparatus includes: generating means; predicting means; projecting means; evaluating means; and estimating means. The generating means generates a kinematics model having joints connected to one another. The predicting means hierarchically calculates predicted positions at a current time of the joints of the objective person, and predicts three-dimensional positions and postures of the joints and the limbs. The projecting means projects the three-dimensional positions and postures of the joints and the limbs of the objective person on a two-dimensional image plane, the three-dimensional positions and the postures being predicted by predicting means. The evaluating means evaluates reliability about projection positions projected by the projecting means based on the observation image of the objective person. The estimating means estimates the three-dimensional positions and postures of the joints and the limbs of the objective person at the current time based on an evaluation result about the reliability.

11 Claims, 11 Drawing Sheets
(1 of 11 Drawing Sheet(s) Filed in Color)

FOREIGN PATENT DOCUMENTS

WO     WO 2005/125210     12/2005

OTHER PUBLICATIONS

K.M. Cheung of al., "Markerless Human Motion Transfer", Proceedings of the 2nd International Symposium on 3D Data Processing, Visualization and Transmission, pp. 373-378, Sep. 2004.

D. Ramanan et al., "Strike a Pose: Tracking People by Finding Stylized Poses". Computer Vision and Pattern recognition (CVPR) San Diego, CA, vol. 1 pp. 271-278, Jun. 2005.

D. Demirdjian et al., "3-D Articulated Pose Tracking for Untethered Diectic Reference", Proceedings of the International Conference on Multimodal interfaces, 2002.

D. Demirdjian et al., "Constraining Human Body Tracking" Proceedings of the International Conference on Computer Vision, 2003, XP002447980.

G. Cheung et al., "Markerless Human Motion Transfer", Proceedings of the 2nd International Symposium on 3D Data Processing Visualization and Transmission, Sep. 2004, XP002447981.

* cited by examiner

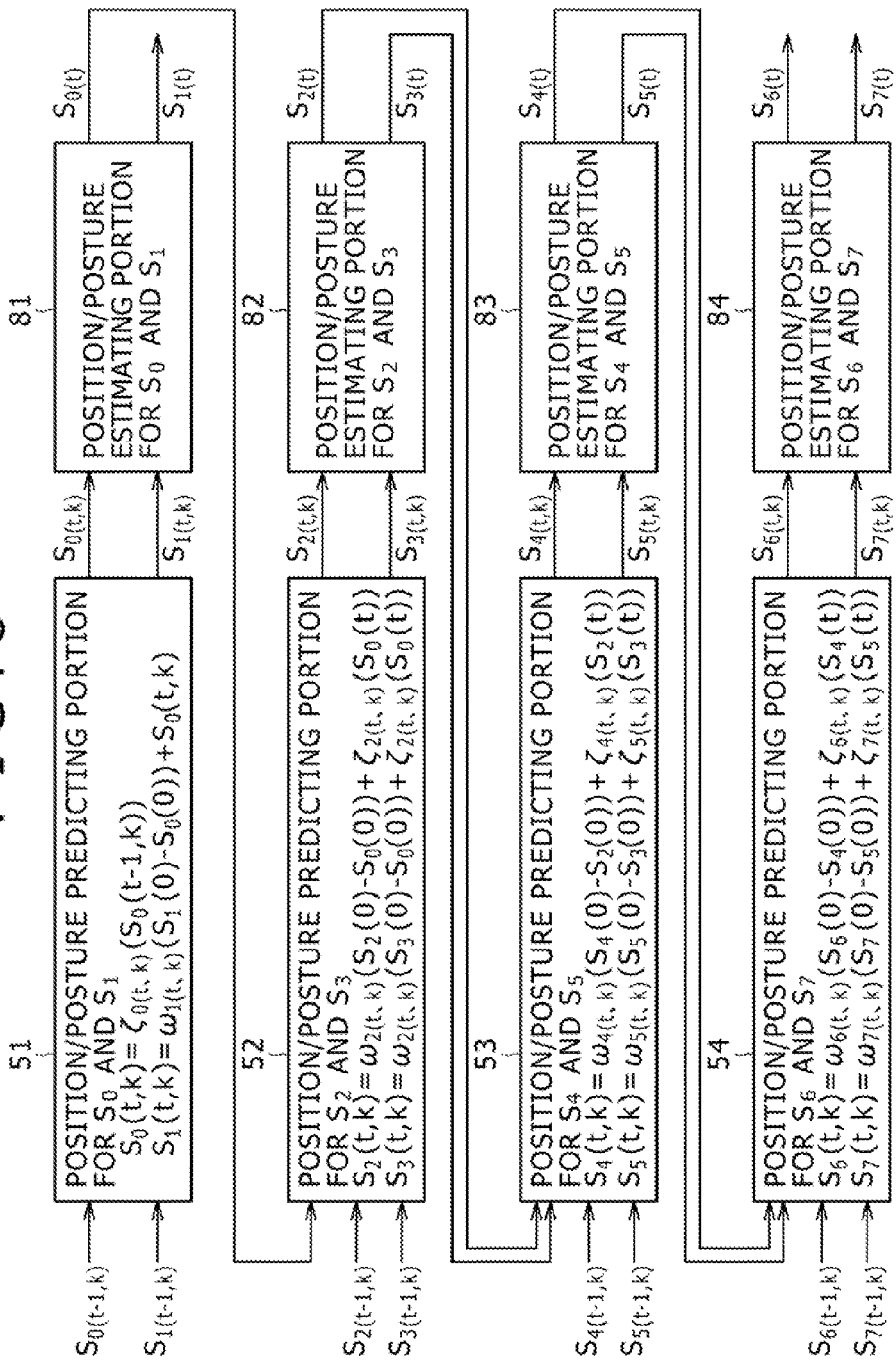

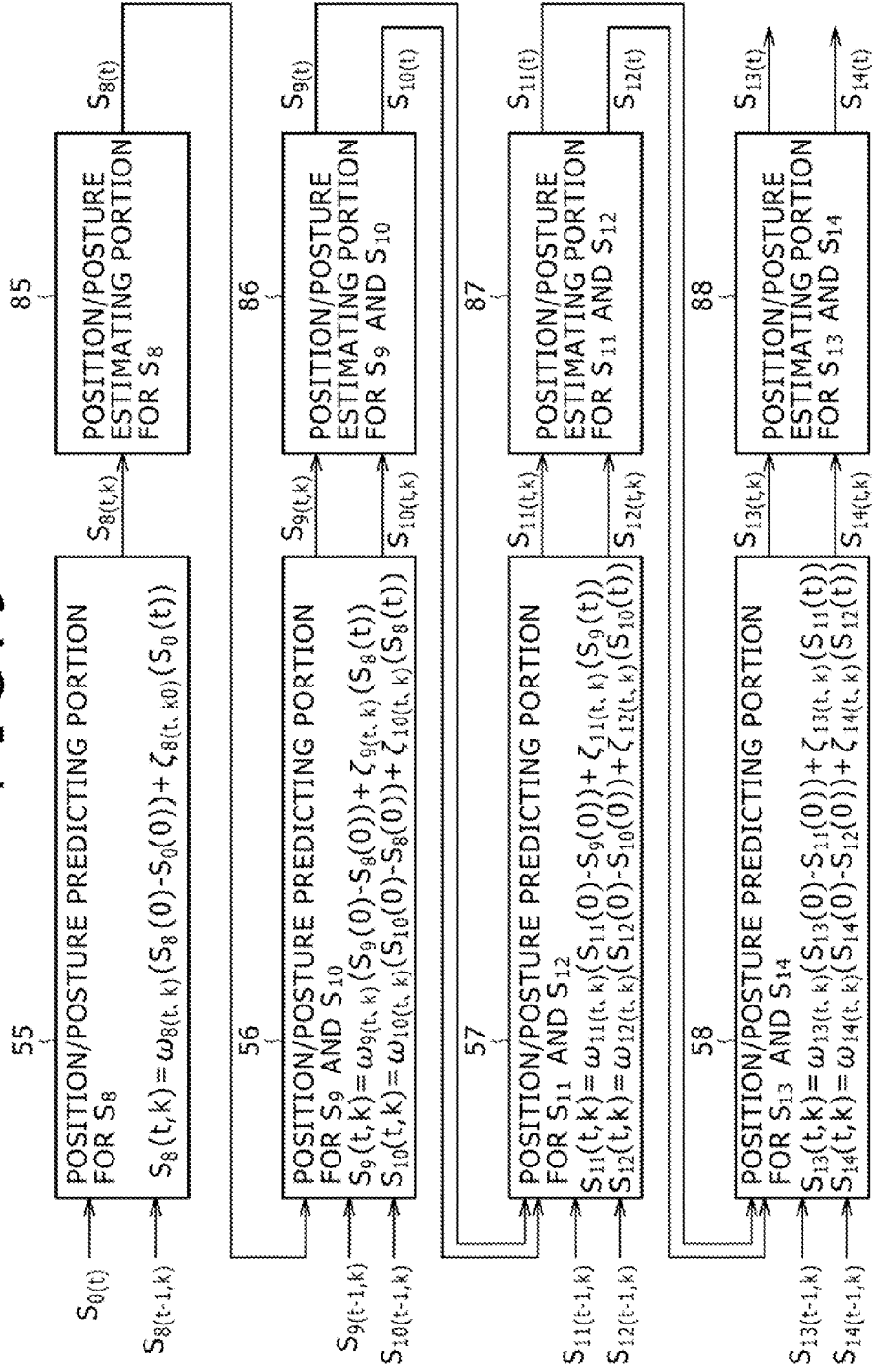

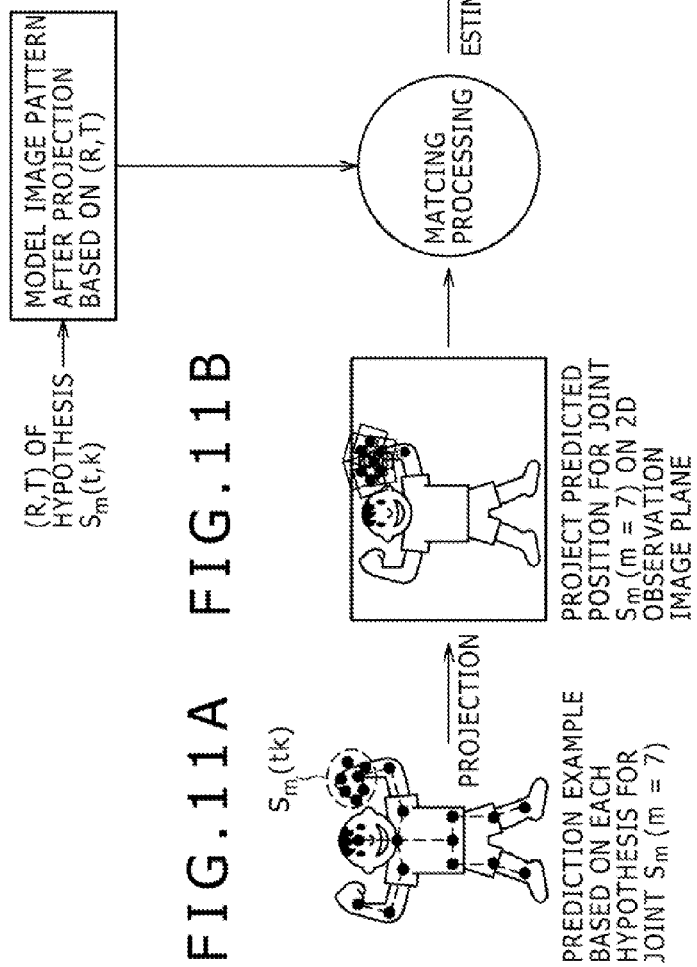

MOTION CAPTURE APPARATUS AND METHOD, AND MOTION CAPTURE PROGRAM

CROSS REFERENCES TO RELATED APPLICATIONS

The present invention contains subject matter related to Japanese Patent Application JP 2006-169070 filed with the Japan Patent Office on Jun. 19, 2006, the entire contents of which being incorporated herein by reference.

BACKGROUND OF THE INVENTION

1. Field of the Invention

The present invention relates to motion capture apparatus and method for recognizing a posture or a motion of an objective person in accordance with an image captured with a camera, and a motion capture program for use therein.

2. Description of the Related Art

It is necessary to realization of a natural interface between a human being and an apparatus to generally analyze information on various actions and voices of an operator, including a manual gesture and a body gesture of a human being, and to detect and recognize existence, intention, and the like of the human being. In order to attain this, the various techniques relating to analysis about a motion and an action of the human being have been investigated in the past. A motion analyzing technique can be roughly classified into a technique for acquiring motion information by using special markers or the like, and a technique for analyzing a motion based on an image analysis not using any of the markers.

A magnetic system, a mechanical system, an optical system, or the like is known as a system using special markers or the like. However, an optical motion capture system is especially frequently utilised as a recent motion tracking/capturing system. Motion capturing/analyzing systems such as an MX camera system (trademark) manufactured by Vicon Peaks Inc., an OptiTrack (trademark) manufactured by Natural Point Inc., and a Hawk Digital System (trademark) manufactured by Motion Analysis Corporation, have already been utilized in the fields of the Computer Graphics (CG), the movie production, and the like. The motion analysing system with markers has such a merit that information on a motion of a person can be previously measured. For this reason, the motion analyzing system with markers is frequently utilized in the fields such as the CG and the movie production for which the highly precise motion analysis is necessary.

However, in this system, a large-scale system configuration is necessary, and attachment of the markers to a human being imposes a burden on the human body. Therefore, it may not be possible to call this system a natural human machine interface (HMI).

Thus, the inventors of the present invention adopt the motion analyzing technique based on the image analysis not using any of the markers in order to realize the natural HMI in the general environment. Several motion analysing techniques each being based on the image analysis not using any of the markers have been investigated. Typically, there is given a motion and posture tracking technique based on a three-dimensional model of a person and a stereo image (for example, D. Demirdjian, T. Ko, T. Darrell, Constraining Human Body Tracking, Proceedings of the International Conference on Computer vision, 2003, hereinafter referred to as Non-patent Document 1). There is also given a person motion tracking technique based on a three-dimensional model of a person using a multiple cameras (for example, K. M. Cheung, S. Baker, J. K. Hodgins, and T. Konade, Markerless Human motion Transfer, Proceedings of the 2nd International Symposium on 3D Data Processing Visualization and Transmission, September, 2004, hereinafter referred to as Non-patent Document 2). There is also given a motion analyzing technique based on a person region and a movement model (for example, Ramanan, D., Forsyth, D A, Zisserman, A. "Strike a Pose: Tracking People by Finding Stylized Poses", Computer Vision and Pattern Recognition (CVPR), San Diego, Calif., Jun. 2005, hereinafter referred to as Non-patent Document 3).

SUMMARY OF THE INVENTION

With the technique described in the Non-patent Document 1, the system configuration is simple, and the motion and posture of the person can be estimated in real time in a limited environment. However, the conditions are necessary such that the technique depends on a precision of a distance image, and an amount of motion between a preceding frame and a subsequent frame is small.

In addition, with the technique described in the Non-patent Document 2, it is expected that, if the three-dimensional model, can be successfully estimated, the estimation precision for a position and a posture of a motion of a person is high. However, a large-scale system configuration is necessary, and also it is necessary to remove a background except for a person in order to precisely construct a three-dimensional model.

In addition, with the technique described in the Non-patent Document 3, an algorithm is simple, and this motion analyzing technique can be utilized in a general background. However, in order to precisely estimate a motion and a posture of a person, it is necessary to precisely detect a region of the limbs of a person.

Also, when these techniques are used, how a model of the body of a human being is applied is a serious problem. In this case, it is expected that an image of an objective person is extracted as a foreground by using Depth information on a parallax image, and a three-dimensional cylinder model is applied thereto. This respect, for example, is described in a Non-patent Document 4 of D. Demirdjian, T. Darrell, 3-D Articulated Pose Tracking for Untethered Diectic Reference, Proceedings of the International Conference on Multimodal Interfaces, 2002. However, with this technique, it is difficult to identify positions of the head and the arms.

As described above, with any of those techniques of the related art, it is difficult to estimate and track the natural motion and posture of the person in the general environment. As a result, it may not be possible to realise the natural HMI.

The present invention has been made in the light of the actual circumstances of the related art as described above, and it is therefore desirable to provide robust motion capture apparatus and method, and a motion capture program each of which is capable of being utilized in an actual environment without relying on a speed of a motion of a person, and a complicated background.

According to an embodiment of the present invention, there is provided a motion capture apparatus for tracking three-dimensional positions and postures of joints, and limbs of an objective person, the motion capture apparatus including: generating means; predicting means; projecting means; evaluating means; and estimating means. The generating means generates a kinematics model having joints connected to one another from an observation image of the objective person. The predicting means hierarchically calculates predicted positions at a current time of the joints of the objective person in accordance with a constraint of coupling among the joints and predicted positions at a preceding time of the joints in the kinematics model, and predicts three-dimensional positions and postures of the joints and the limbs of the objective person at the current time. The projecting means projects the three-dimensional positions and postures of the joints and the limbs of the objective person at the current time on a two-dimensional image plane, the three-dimensional positions and postures being predicted by predicting means. The evaluating means evaluates reliability about projection positions projected by the projecting means in accordance with the observation image of the objective person. The estimating means estimates the three-dimensional positions and postures of the joints and the limbs of the objective person at the current time in accordance with an evaluation result about the reliability.

In addition, according to another embodiment of the present invention, there is provided a motion capture method of tracking three-dimensional positions and postures of joints and limbs of an objective person, the motion capture method including the steps of: generating; hierarchically calculating and predicting; projecting; evaluating; and estimating. The generating step generates a kinematics model having joints connected to one another from an observation image of the objective person. The hierarchically calculating and predicting step calculates predicted positions at a current time of the joints of the objective person in accordance with a constraint of coupling among the joints and predicted positions at a preceding time of the joints in the kinematics model, and predicts three-dimensional positions and postures of the joints and the limbs of the objective person at the current time. The projecting step projects the three-dimensional positions and postures of the joints and the limbs of the objective person at the current time on a two-dimensional image plane, the three-dimensional positions and postures being predicted in the predicting step. The evaluating step evaluates reliability about projection positions projected in the projecting step in accordance with the observation image of the objective person. The estimating step estimates the three-dimensional positions and postures of the joints and the limbs of the objective person at the current time in accordance with an evaluation result about the reliability.

Also, according to still another embodiment of the present invention, there is provided a motion capture program for executing processing for tracking three-dimensional positions and postures of joints and limbs of an objective person, the motion capture program including the steps of: generating; hierarchically calculating and predicting; projecting; evaluating; and estimating. The generating step generates a kinematics model having joints connected to one another from an observation image of the objective person. The hierarchically calculating and predicting step calculates predicted positions at a current time of the joints of the objective person in accordance with a constraint of coupling among the joints and predicted positions at a preceding time of the joints in the kinematics model, and predicts three-dimensional positions and postures of the joints and the limbs of the objective person at the current time. The projecting step projects the three-dimensional positions and postures of the joints and the limbs of the objective person at the current time on a two-dimensional image plane, the three-dimensional positions and postures being predicted in the predicting step. The evaluating step evaluates reliability about projection positions projected in the projecting step in accordance with the observation image of the objective person. The estimating step estimates the three-dimensional positions and postures of the joints and the limbs of the objective person at the current time in accordance with an evaluation result about the reliability.

According to the embodiments of the present invention, the kinematics model having the joints connected to one another is generated from the observation image of the objective person. Further, the predicted positions at the current time of the joints of the objective person are hierarchically calculated in accordance with the constraint of coupling among the joints and the predicted positions at the preceding time of the joints in the kinematics model, and the three-dimensional positions and postures of the joints and the limbs of the objective person at the current time are predicted. Still further, the three-dimensional positions and postures of the joints and the limbs of the objective person at the current time are projected on the two-dimensional image plane, the three-dimensional positions and postures being predicted. Also, the reliability about the projection positions is evaluated in accordance with the observation image of the objective person; and the three-dimensional positions and postures of the joints and the limbs of the objective person at the current time are estimated in accordance with the evaluation result about the reliability. As a result, it is possible to realise the natural human machine interaction for which any of the special marker sensors is unnecessary.

BRIEF DESCRIPTION OF THE DRAWINGS

The application file contains at least one drawing executed in color. Copies of this patent application publication with color drawing will be provided by the Office upon request and payment of the necessary fee.

FIG. 8 is a block diagram showing a structure for predicting positions of joints of the kinematic model;

FIG. 9 is another block diagram showing a structure for predicting positions of joints of the kinematic model;

FIGS. 11A to 11C are respectively schematic views explaining processing in a posture/position projecting portion, a reliability evaluating portion, and a posture/position estimating portion.

DETAILED DESCRIPTION OF THE PREFERRED EMBODIMENTS

Preferred embodiments of the present invention will be described in detail hereinafter with reference to the accompanying drawings.

Figure 1:
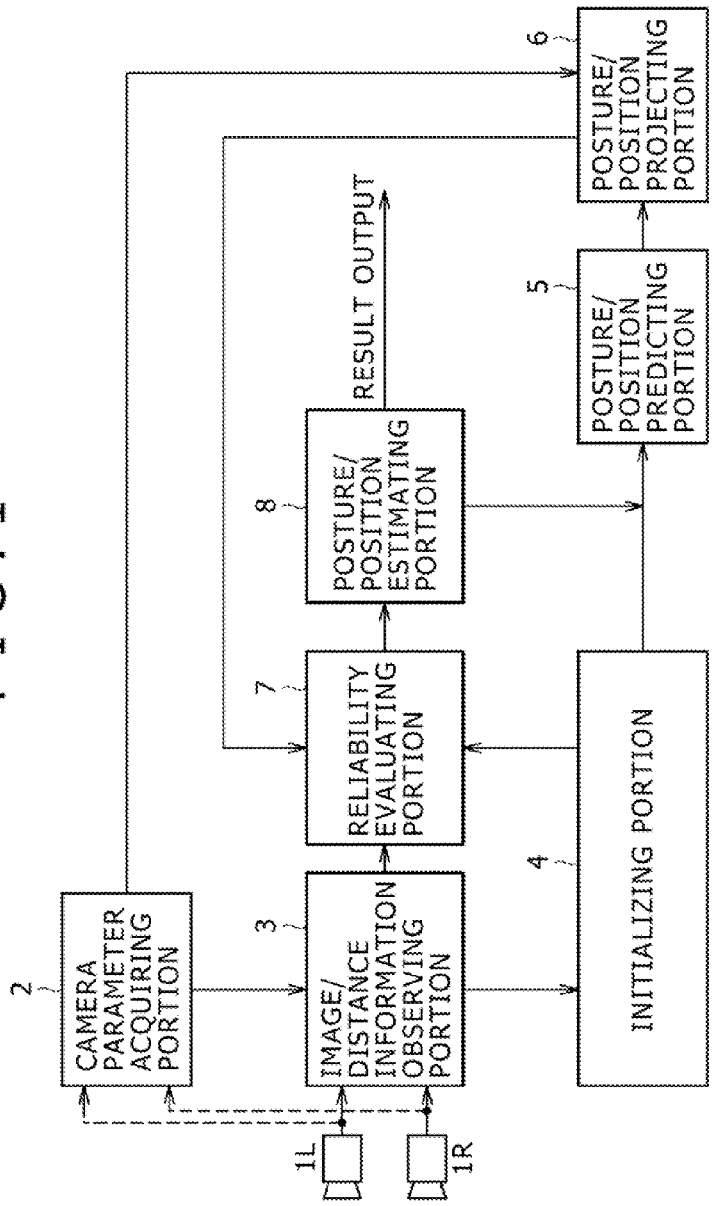
FIG. 1 is a block diagram snowing a configuration of a motion capture apparatus according to an embodiment of the present invention.

FIG. 1 is a block diagram showing a configuration of a motion capture apparatus according to an embodiment of the present invention. The motion capture apparatus includes cameras 1L and 1R which are disposed in predetermined positions, respectively, a camera parameter acquiring portion 2, an image/distance information observing portion 3, and an initializing portion 4. Also, the motion capture apparatus includes a posture/position predicting portion 5, a posture/position projecting portion 6, a reliability evaluating portion 7, and a posture/position estimating portion 8. Here, the camera parameter acquiring portion 2 acquires camera parameters through a camera calibration. The image/distance information observing portion 3 observes information on images and distances captured with the cameras 1L and 1R, respectively. The initializing portion 4 generates a kinematics model having joints coupled to one another, and preserves image information. Also, the posture/position estimating portion 5 predicts a posture and a position of an objective person at a current time. The posture/position projecting portion 6 projects the predicted posture and position on a two-dimensional image plane. The reliability evaluating portion 7 evaluates the two-dimensional position obtained through the projection and generates an evaluation value. The posture/position estimating portion 8 estimates a posture and a position of the objective person at the current time in accordance with the evaluation value.

The cameras 1L and 1R are disposed in the predetermined positions, respectively, so that the same objective person can be photographed with these cameras 1L and 1R. Mote that, in this embodiment, the motion capture apparatus will now be described on the assumption that it uses "a stereo vision" for calculating a distance to the object from a parallax between two cameras. However, the motion capture apparatus of this embodiment, for example, may utilise "a laser range finder" or the like. In this case, the laser range finder measures a time until a reflected light of a laser beam applied to an object is detected, thereby calculating a distance to the object.

The camera parameter acquiring portion 2 acquires the camera parameters in accordance with which the real world coordinates and the camera image coordinates are associated with each other through the camera calibration. Also, the camera parameter acquiring portion 2 outputs the resulting camera parameters to each of the image/distance information observing portion 3, and the posture/position projecting portion 6.

The image/distance information observing portion 3 outputs information on images captured with the cameras 1L and 1R, respectively, to each of the initializing portion 4 and the reliability evaluating portion 7. In addition, the image/distance information observing portion 3 generates distance information in accordance with the camera parameters acquired by the camera parameter acquiring portion 2, and outputs the resulting distance information to each of the initializing portion 4 and the reliability evaluating portion 7.

The initializing portion 4 obtains three-dimensional coordinates (x, y, z) of each of joint points $S_k$ of the objective person in order to generate a kinematics model. Also, the initializing portion 4 preserves image information (initial image model) on feature points such as the joint points, the limbs among the joint points, and a face in order to evaluate the predicted postures and positions. This kinematics model is a joint model having the joints coupled to one another. Note that, in this embodiment, the motion capture apparatus is described below on the assumption that the kinematics model represented by fifteen joint points of $\{S_k: k=0, 1, \ldots, 14\}$. In addition, texture information represents a texture of a surface, color information, parallax information, a reliability evaluation value about contours, and the like, for example, can be used as the image information.

The posture/position estimating portion 5 hierarchically predicts the positions of the joints and the limbs at a current time of the objective person in accordance with a probability model by using the predicted positions of the joints and the limbs at a preceding time of the objective person, and a constraint of coupling among the joints of the kinematics model, thereby predicting the posture of the body. More specifically, as will be described later, the predicted positions of the joints of a preceding hierarchy of the joint model are given a probability distribution, and predicted positions of the joints of a next hierarchy is arithmetically operated.

The posture/position projecting portion 6 projects the predicted positions and postures of the joints and the limbs in the three-dimensional space of the objective person at the current time on a two-dimensional image plane in accordance with a projection matrix P, thereby obtaining projection positions (u, v) on the two-dimensional image plane corresponding to the three-dimensional coordinates (x, y, z). Here, the predicted positions and postures of the joints and the limbs in the three-dimensional space of the objective person at the current time are predicted by the posture/position predicting portion 5. Also, the projection matrix P is obtained through the camera calibration.

The reliability evaluating portion 7 calculates similarity between the image information (such as distance information, color information, and texture information) on projection positions (u, v) on the two-dimensional image (observed image) plane obtained by the posture/position projecting portion 6, and the previously preserved image information (initial image model). As a result, the reliability evaluating portion 7 evaluates properness of the projection positions.

The posture/position preserving portion 8 estimates the positions and the postures in the three-dimensional space of the objective person at the current time in accordance with the evaluation value for the projection positions on the two-dimensional image evaluated by the reliability evaluating portion 7. The estimation information on the positions and the postures in the three-dimensional space of the objective person at the current time is outputted as information on the positions of the joints and the limbs of the objective person at a preceding time to the posture/position predicting portion 5.

Here, an outline of the above-mentioned motion capture processing will now be described with reference to schematic views shown in FIGS. 2A to 2E.

Firstly, at least two or more cameras 1L and 1R are previously disposed so that the same objective person can be photographed with the at least two or more cameras 1L, and 1R. Then, the camera parameter acquiring portion 2 acquires a positional relationship between the at least two or more cameras 1L and 1E, the camera parameters, and the like through the camera calibration. The camera parameter acquiring portion 2 outputs the camera parameters and the like to each of the image/distance information observing portion 3 and the posture/position projecting portion 6.

Figure 2:
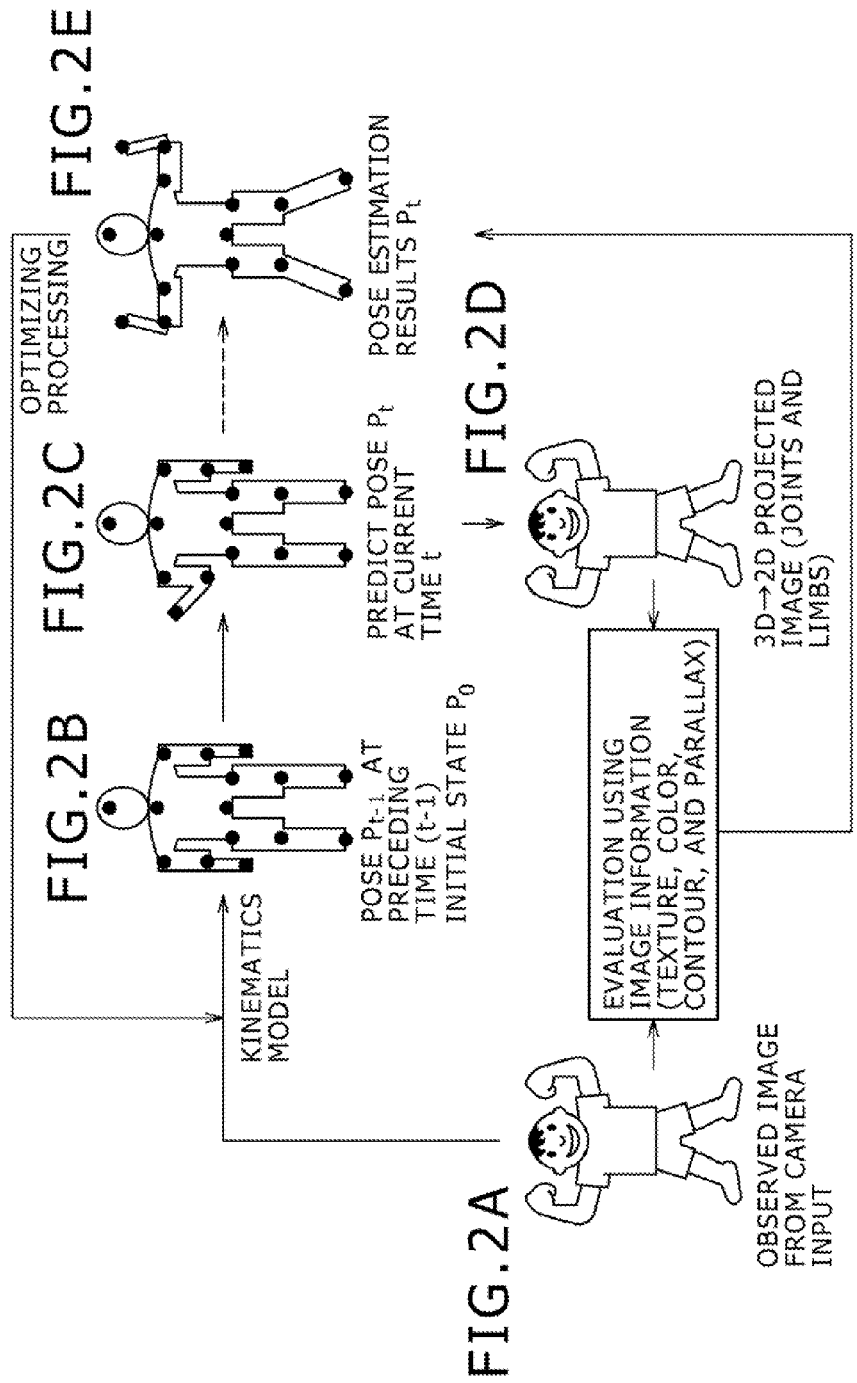
FIGS. 2A to 2E are respectively schematic views explaining an outline of motion capture processing executed in the motion capture apparatus according to the embodiment of the present invention.

The initializing portion 4 predicts a parallax image (u, v, depth) from the observation image, as shown in FIG. 2A, of the objective person the information on which is outputted from the image/distance information observing portion 3. Also, the initializing portion 4 inversely projects the resulting parallax image (u, v, depth) on the three-dimensional space to calculate the three-dimensional position/coordinate model (x, y, z) about the three-dimensional shape and the joints of the objective person, thereby generating the kinematics model. Also, the initializing portion 4 preserves information on the images of the joints (initial image model) in accordance with the observation image.

Next, the posture/position predicting portion 5 hierarchically predicts positions/postures $P_t$ of the joints at a current time t as shown in FIG. 2C in accordance with the estimation results about positions/postures $P_{t-1}$ of the joints at a preceding current (t−1) as shown in FIG. 2B and in accordance with the probability model by using the constraint of the coupling among the joints of the kinematics model.

The posture/position projecting portion 6 projects the predicted positions/postures of the joints of the objective person at the current time t on the two-dimensional image plane as shown in FIG. 2D in accordance with the projection matrix P obtained through the camera calibration. As a result, the posture/position projecting portion 6 obtains the projection positions and the parallax (u, v, depth) on the two-dimensional image plane corresponding to the three-dimensional coordinates (x, y, z).

Also, the reliability evaluating portion 7 calculates the similarity between the image information such as the parallax (n, v, depth) of the projection positions projected on the two-dimensional image plane (observed image), the color information, and the texture information, and the previously preserved image information (initial image model). As a result, the reliability evaluating portion 7 evaluates the properness of the projection positions/postures of the joints of the objective person projected on the two-dimensional image plane.

The posture/position estimating portion 8 finally obtains the predicted positions/postures $P_t$ in the three-dimensional space of the objective person at the current time t as shown in FIG. 2E.

The position, posture, and motion tracking of the objective person are performed in such a manner, thereby making it possible to realize the natural human machine interface (HMI) in which no burden is imposed on the objective person.

Figure 3:
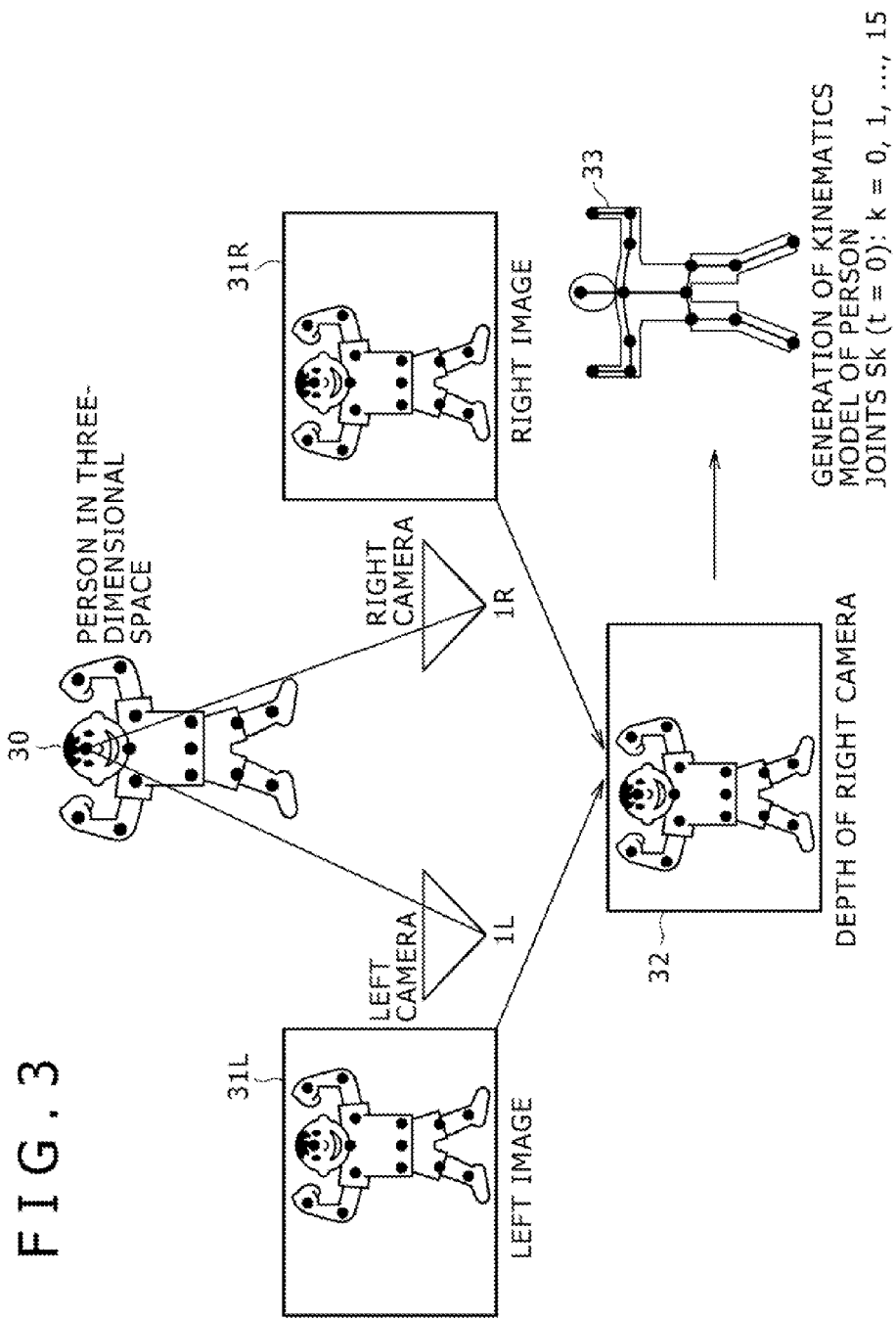
FIG. 3 is a schematic view explaining an outline of processing for generating a kinematics model of an objective person.

Subsequently, processing executed in the above-mentioned motion capture apparatus will now be described in detail with reference to FIG. 3. Firstly, a description will now be given with respect to the generation of the kinematics model of the objective person. As shown in FIG. 3, images of an objective person 30 in the three-dimensional space are observed with the previously calibrated left-hand and right-hand side cameras 1L and 1E, respectively. Also, a parallax image 32 is estimated by using these observed images (u, v, depth) 31L and 31R. Also, the parallax image (u, v, depth) 32 is projected on the three-dimensional space in accordance with a projection matrix obtained through the camera calibration, and coordinate positions (x, y, z) of the joints of the objective person in the three-dimensional space are obtained. As a result, it is possible to generate a kinematics model 33 of the objective person.

Figure 4:
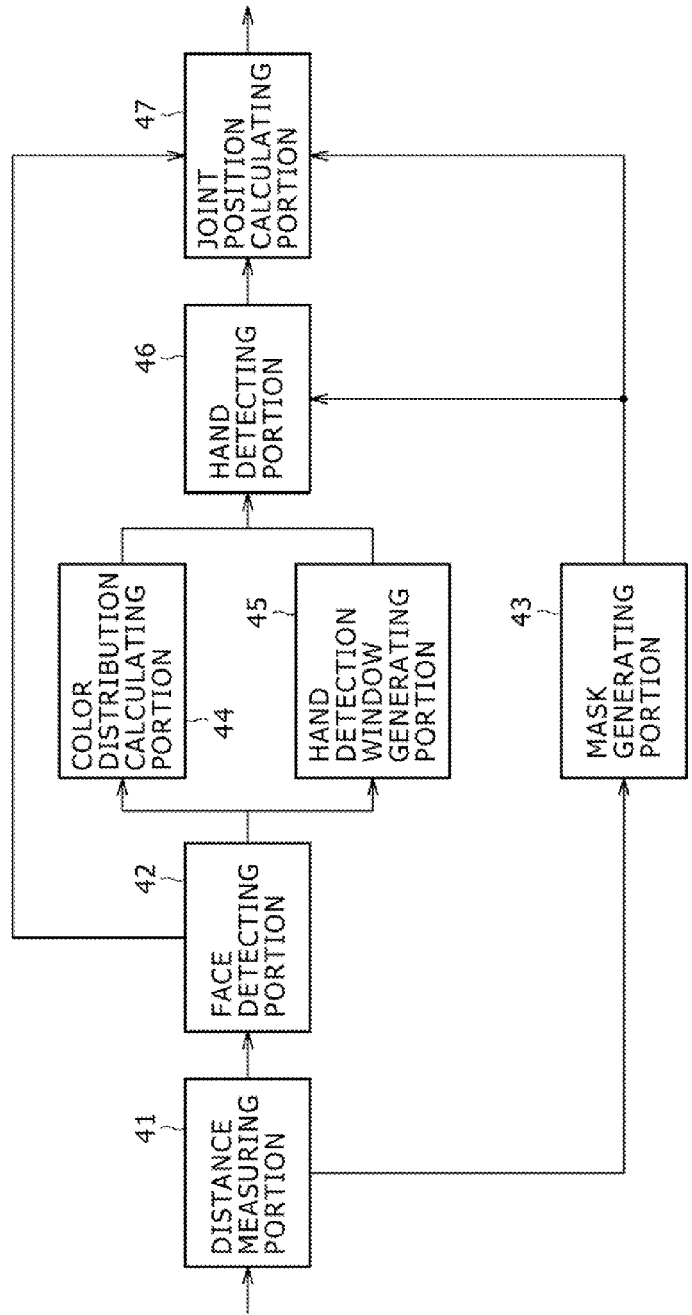
FIG. 4 is a block diagram showing a configuration of an initializing portion for generating the kinematics model in the motion capture apparatus shown in FIG. 1.

FIG. 4 is a block diagram showing a configuration of the initializing portion 4 for initializing the kinematics model. The initializing portion 4 includes a distance measuring portion 41, a face detecting portion 42, a mask generating portion 43, a color distribution calculating portion 44, a hand detection window generating portion 45, a hand detecting portion 46, and a joint position calculating portion 47. Here, the distance measuring portion 41 generates a distance image. The face detecting portion 42 detects a position and a distance to a face region from an input image. The mask generating portion 43 generates a mask image with an object person as a foreground in accordance with the distance image and a distance to a face. The color distribution calculating portion 44 calculates a color histogram about the face region. The hand detection window generating portion 45 calculates window positions exhibiting positions where hands should be located in accordance with the position and the distance to the face region. The hand detecting portion 46 detects the hands in accordance with a hue and a color saturation of the face region, variances of the hue and the color saturation, positions of the hand detection windows, and the mask image. Also, the joint position calculating portion 47 calculates the position of the joints in accordance with the position and the distance to the face, and the positions and the distances to the hands.

Figure 5:
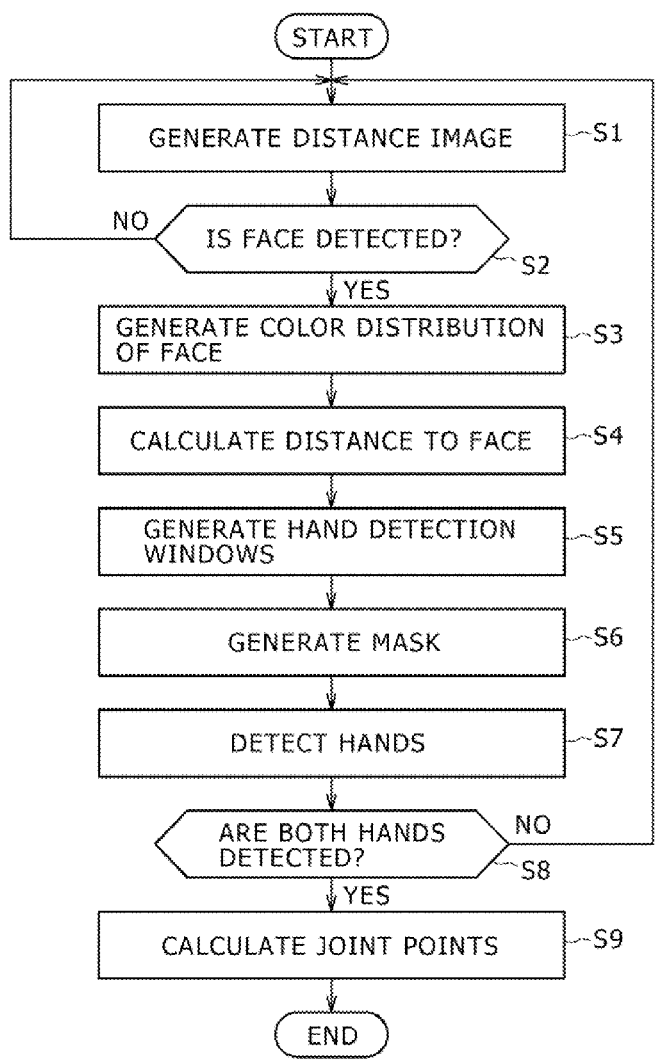
FIG. 5 is a flow chart showing initializing processing executed in the initializing portion shown in FIG. 4.

Subsequently, an operation for initializing processing executed in the initializing portion 4 will now be described with reference to a flow chart shown in FIG. 5, and schematic views shown in FIGS. 6A to 6F.

In Step S1, the distance measuring portion 41 generates a distance image in accordance with image/distance information outputted from the image/distance information observing portion 3. Here, preferably, the distance measuring portion 41 generates an image representing the reliability of the distance about the distance image at the same time that the distance image is generated. As a result, it is possible to improve the precision for mask image generation which will be described later. Note that, for example, when a distance is calculated by utilising the stereo method, and matching is performed by using a normalized correlation, an index number in the form of which the matching cost is expressed can be used as the reliability.

Figure 6A:
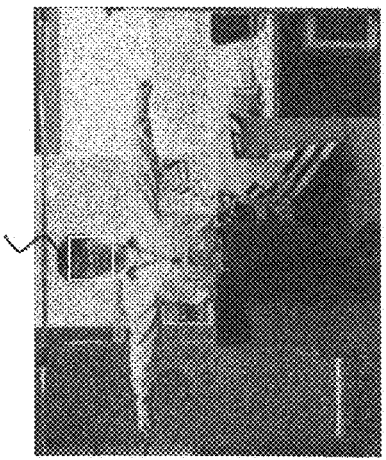
FIGS. 6A to 6F are respectively views explaining the initializing processing executed in the initializing portion shown in FIG. 4.

In Step S2, the face detecting portion 42, as shown in FIG. 6A, detects a face F from an input image of an objective person. When it is decided that the face F is detected, the operation proceeds to processing in Step S3. On the other hand, when it is judged that no face F is detected, the operation returns back to the processing in Step S1.

A technique for extracting an amount of face features by using a Gabor filter, and performing face discrimination by using a support vector machine can be used as the face recognizing technique. This technique, for example, is described in WO2003/019475, (Domestic Re-publication of PCT International Publication for patent application), (entitled "Robot Apparatus, and Face Recognizing Method and Apparatus" and assigned to SONY Corporation).

Figure 6B:
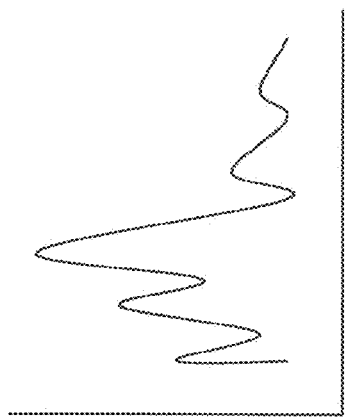

In Step S3, the color distribution calculating portion 44, as shown in FIG. 6B, calculates a histogram about colors of the face region detected by the face detecting portion 42. Here, in the histogram, with respect to a hue (H) and a color saturation (S) of an HSI color specification system, the H having the highest frequency, and the S having the highest frequency are obtained, and are given suitable variances, respectively. Thus, the resulting values are outputted.

Figure 6C:

In Step S4, the face detecting portion 42, as shown in FIG. 6C, calculates a distance to the face in accordance with the detected face F, and the distance image measured by the distance measuring portion 41. Here, in order to remove an influence of noises, it is preferable not to use an average value, but to use a medium as a value of the distance to a center of the face region.

Figure 6D:
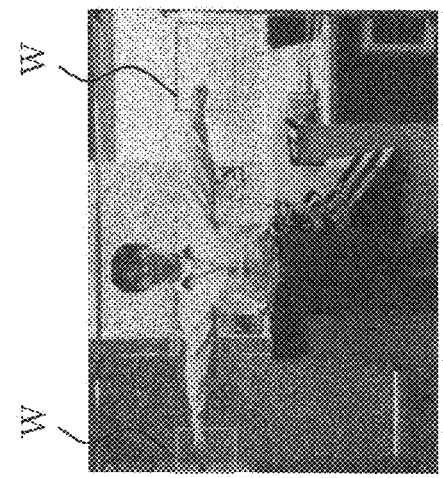

In Step S5, the hand window generating portion 45, as shown in FIG. 6D for example, calculates positions of windows W exhibiting positions where the hands should be located when the objective person horizontally extends his arms in accordance with the position and the distance to the face region detected by the face detecting portion 42. In this method of generating the hand detection windows, firstly, the position and the distance to the face in the image are transformed into the world coordinate system in accordance with the camera parameters or the like acquired by the camera parameter acquiring portion 2. Also, lengths of the neck and the arms from the face position are added to each other, thereby determining each of the window positions. Mote that, the length of the neck is prescribed in the range of 270±150 mm, and the length of each of the arms is prescribed in the range of 900±350 mm in consideration of differences among individuals. In addition, it is assumed that the objective person stands approximately in front of the motion capture apparatus, and it is supposed that the distance to each of the hands is approximately equal that to the face. The world coordinate values of the hand detection windows obtained in the manner as described above are inversely transformed into the camera coordinate system, thereby calculating the positions of the hand detection windows in the image.

Figure 6E:
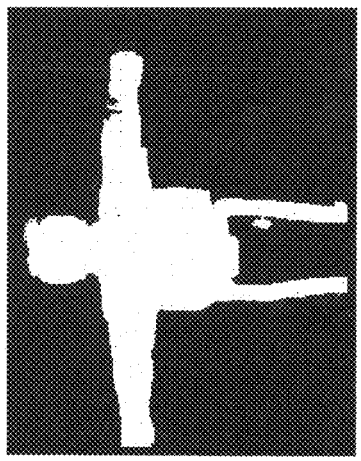

In Step 36, the mask generating portion 43 generates a mask image with the objective person shown in FIG. 6E as the foreground in accordance with the distance image generated by the distance measuring portion 41, and the distance to the surface calculated by the face detecting portion 42. Here, when an image representing reliability about a distance is generated in the distance measuring portion 41, the mask generating portion 43 generates an image which is binarized using a value shifted from the distance to the face by a given distance as a threshold by using the reliability about the distance. As a result, it is possible to improve the precision for generation of the mask image. Moreover, the histogram is obtained by labeling the image, and only the regions each having the large frequency is left, thereby making it possible to remove the noises.

In Step S7, the hand detecting portion 46 detects the hands in accordance with the hue and the color saturation calculated by the color distribution calculating portion 44, the variances of the hue and the color saturation, the positions of the windows generated by the hand detection window generating portion 45, and the mask image generated by the mask generating portion 43. More specifically, the regions each failing within the range having the same hue and color saturation as those of the face as detected as the hands from the region becoming the foreground in the mask image in the hand detecting windows. Here, a circle is applied to a right-hand end in the case of the right hand in the hand region, or a circle is applied to a left-hand end in the case of the left hand in the hand region. Thus, the hand detecting portion 46 outputs the central position as the coordinates of the hand. In addition, a value of the distance in the central coordinates within the hand region is outputted as information on the distance to each of the hands.

In Step S8, the hand detecting portion 46 decides whether or not both the hands are detected. When it is decided that both the hands are detected, the initialization is decided to succeed, and the operation proceeds to processing in Step S9. On the other hand, when it is decided that both the hands are not detected, the operation returns back to the processing in Step S1.

Figure 6F:
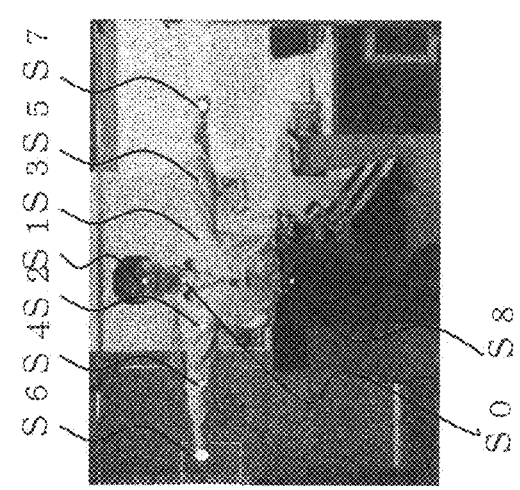

In Step S9, the joint position calculating portion 47 calculates the positions of the joints in accordance with the position and the distance to the face detected by the face detecting portion 42, and the positions and the distances to the hands detected by the hand detecting portion 46. FIG. 6F shows an image representing positions $S_1$ to $S_8$ of the joints. In this embodiment, since the assumption that the hands are calculated in a horizontal state is adopted, the positions of the shoulders and the elbows can be determined by using the positions of both the hands, and a ratio in length among the shoulders, the upper arm and the lower arm which is previously prepared. Moreover, the noises can be removed and the precision about the positions of the elbows and the shoulders can be improved by using the mask image which is generated by the mask generating portion 43 and which represents the reliability about the distance. More specifically, firstly, a Y coordinate of the mask foreground portion in an X coordinate of the elbow, and a medium thereof is adopted as a Y coordinate. In addition, several points are sampled in the X coordinates of the upper arm, and the medium of the Y coordinates of the mask foreground portion in the respective sampled points is adopted as the Y coordinate of the point concerned. Also, an approximate straight line of the upper arm portion is obtained by using these points. Also, a point failing on the approximate straight line in the X coordinate of the shoulder is adopted as the shoulder position. The precision for the joint positions can be greatly improved through the above processing.

The joint positions in the three-dimensional space are obtained in the manner described above, which results in that the kinematics model can be initialized with high precision. Also, during the initialization of the kinematics model, the image information (such as the texture, the color, the parallax, and the reliability evaluation value) corresponding to the joint points of the kinematics model is preserved and is set as an initial image model. The initial image model is compared with the observed image in tracking processing which will be described later, and is used for evaluation of the properness of the prediction, and for calculation of the tracking results.

Figure 7A:
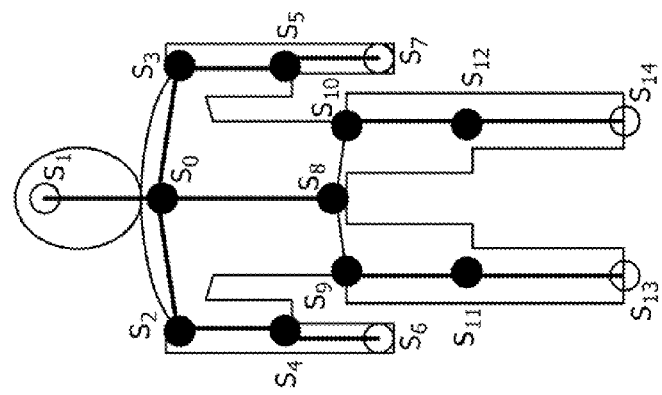
FIGS. 7A and 7B are respectively views explaining a hierarchically predicting method in the embodiment of the present invention.

Next, a description will now be given with respect to a method of predicting the joint positions of the kinematics model. FIG. 7A shows a conceptual view explaining a hierarchically predicting method in this embodiment of the present invention. With this hierarchically predicting method, firstly, a position of a joint $S_0$ of the neck, and a position of a head center $S_1$ are estimated by using information on the head (face) of a person which is easiest to observe. Also, positions of joints $S_2$, and $S_3$ of the shoulders, and a position of a joint $S_8$ of the back are estimated in accordance with the estimation results about the joint $S_0$ of the neck. After that, positions of joints $S_4$ and $S_5$ of both the elbows, and positions of joints $S_9$ and $S_{10}$ of the waist are estimated by using the estimation results about the joints $S_2$, $S_3$ and $S_8$. Moreover, positions of joints $S_6$ and $S_7$ of both the arms are estimated on the basis of the joints $S_4$ and $S_5$ of both the elbows. Also, positions of joints $S_{11}$ and $S_{12}$ of both the knees are estimated on the basis of the joints $S_9$ and $S_{10}$ of the waist. Finally, positions of joints $S_{13}$ and $S_{14}$ of both the feet are estimated on the basis of the joints $S_{11}$ and $S_{12}$ of both the knees. That is to say, the hierarchically predicting method is such that the joint positions at the current time are successively calculated in accordance with the constraint of the coupling among the joints, and the joint positions at the preceding time in the kinematics model.

Figure 7B:
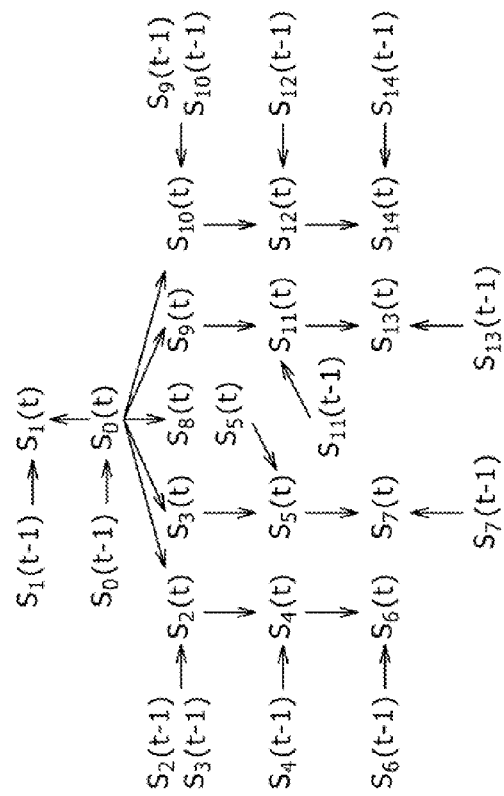
Figure 10:
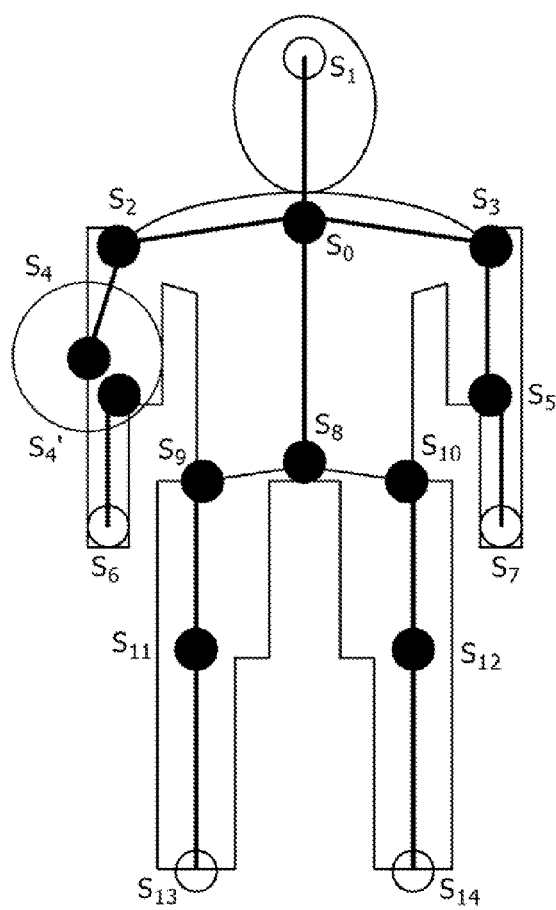
FIG. 10 is a schematic view explaining an example of processing for evaluating reliability of results about tracking of a preceding joint point $S_{k-1}$, and dynamically changing a prediction model of a current joint point $S_k$.

FIG. 7B is a schematic view explaining a method of predicting the joint points. The predicted positions of the joints $S_1$ to $S_{14}$ at the current time (t) are obtained in accordance with the prediction results at the preceding time (t−1). In addition, the predicted position of each of the joints at the current time (t) is expressed in the form of a normal distribution. Thus, the evaluation of the reliability (probability) is performed for such a predicted position. Also, the estimation results about each of the joints are made to fluctuate within a certain range in accordance with the evaluation value about the reliability. As a result, when the estimation results having the poor precision are utilized as they are, a large influence is prevented from being exerted on each of the estimation precision for the joints adjoining each other.

FIGS. 8 and 9 are respectively block diagrams each showing a constitution for prediction of each of the joint positions in the kinematics model. Here, each of position/posture predicting portions 51 to 58 for the joints $S_0$ to $S_8$ corresponds to the posture/position predicting portion 5 shown in FIG. 1. Also, each of position/posture predicting portions 81 to 88 for the joints $S_0$ to $S_8$ corresponds to the posture/position estimating portion 8 shown in FIG. 1. That is to say, referring now to FIG. 1, in order corresponding to the constraint of the coupling among the joints in the kinematics model, the predicted positions of the joints are predicted in the posture/position predicting portion 5, and the predicted positions are projected on the two-dimensional image plane in the posture/position projecting portion 6. Also, in that order, the reliability about the predicted positions projected on the two-dimensional image plane is evaluated in the reliability evaluating portion 7, and the estimated positions are estimated in the posture/position estimating portion 8 in accordance with the evaluation results. In addition, the estimated positions estimated in the posture/position estimating portion 8 are used in the arithmetic operation for the prediction of the positions of the joints in the hierarchy which will be predicted next time.

The predicted values (positions and postures) of the joints at the current time t are calculated by using a prediction function $\omega_{m(t, k)}$ the posture, and a prediction function $\xi_{m(t, k)}$ for position. Here, the prediction function $\omega_{m(t, k)}$ for the posture, and the prediction function $\xi_{m(t, k)}$ for position are based on hypotheses $\{k=1, 2, \ldots, K\}$ for the joints $S_m$ (m=0, ..., 14) at the preceding time (t−1). The prediction functions $\omega_{m(t, k)}$ and $\xi_{m(t, k)}$ are calculated with respect to the m-th joint at the time t by using Expressions (1) and (2), respectively:

$$\omega_{m(t,k)} = S^\omega_m(t-1,k) + \phi(\mu_{m1}, \sigma_{m1}) + X_{m1} v^\omega_{(t-1)} \quad (1)$$

$$\xi_{m(t,k)} = S^\xi_m(t-1,k) + \phi(\mu_{m2}, \sigma_{m2}) + \kappa_{m2} v^\xi_{(t-1)} \quad (2)$$

where $\Phi$ is a function for obtaining a normal random number about an average value $\mu$, and a standard variance $\sigma$, $v$ represents a motion speed of each of the joints at the preceding time (t−1), and $\kappa$ represents a constant used to adjust the degree of a contribution.

The constitution for prediction of each of the joints of the upper half of the body shown in FIG. 8 includes a position/posture predicting portion 51 for $S_0$ and $S_1$, a position/posture estimating portion 81 for $S_0$ and $S_1$, a position/posture predicting portion 52 for $S_2$ and $S_3$, a position/posture estimating portion 82 for $S_2$ and $S_3$, a position/posture predicting portion 53 for $S_2$ and $S_5$, a position/posture estimating portion 83 for $S_4$ and $S_5$, a position/post are predicting portion 54 for $S_6$ and $S_7$, and a position/posture estimating portion 84 for $S_8$ and $S_7$. Here, the position/posture predicting portion 51 for $S_0$ and $S_1$ predicts the position and posture of the joint $S_0$ of the neck, and the position and posture of the center $S_1$ of the head. The position/posture predicting portion 52 for $S_2$ and $S_3$ predicts the positions and postures of the joints $S_2$ and $S_3$ of the shoulders in accordance with the estimation results about the joint $S_0$ of the neck. The position/posture predicting portion 53 for $S_4$ and $S_5$ predicts the positions and the postures of the joints $S_4$ and $S_5$ of both the elbows in accordance with the estimation results about the joints $S_2$ and $S_3$ of the shoulders. Also, the position/posture predicting portion 54 for $S_6$ and $S_7$ predicts the positions and the postures of the joints $S_8$ and $S_7$ of both the arms in accordance with the estimation results about the joints $S_4$ and $S_5$ of both the elbows.

The position/posture predicting portion 51 for $S_0$ and $S_1$ receives as its inputs information on the joint position $S_{0(t-1, k)}$ at the preceding time (t−1) of the neck, and information on the head central position $S_{1(t-1, k)}$ at the preceding time (t−1). Also, the position/posture predicting portion 51 for $S_0$ and $S_1$ calculates the predicted values of the joint position $S_{0(t, k)}$ of the neck, and the head central position. $S_{1(t, k)}$ at the current time (t) by using Expressions (3) and (4):

$$S_0(t,k) = \xi_{0(t,k)}(S_0(t-1,k)) \quad (3)$$

$$S_1(t,k) = \omega_{1(t,k)}(S_1(0) - S_0(0)) + S_0(t,k) \quad (4)$$

The position/posture estimating portion 81 for $S_0$ and $S_1$ evaluates the reliability about the hypotheses $\{k=1, 2, \ldots, K\}$ for the joint position $S_{0(t, k)}$ of the neck, and the head central position $S_{1(t, k)}$ at the current time (t) as will be described later. Also, the position/posture estimating portion 81 for $S_0$ and $S_1$, for example, outputs the hypothesis $S_{0(t)}$ for the joint position of the neck having the highest reliability to the position/posture predicting portion 52 for $S_2$ and $S_3$.

The position/posture predicting portion 52 for $S_2$ and $S_3$ receives as its inputs information on the joint position $S_{2(t-1, k)}$ and $S_{3(t-1, k)}$ of the shoulders at the preceding time (t−1), and information on the estimated position $S_{0(t)}$ of the joint of the neck at the current time (t). Also, the position/posture predicting portion 52 for $S_2$ and $S_3$ calculates the predicted values of the joint positions $S_{2(t, k)}$ and $S_{3(t, k)}$ of the shoulders at the current time ht) by using Expressions (5) and (6):

$$S_2(t,k) = \omega_{2(t,k)}(S_2(0) - S_0(0)) + \xi_{2(t,k)}(S_0(t)) \quad (5)$$

$$S_3(t,k) = \omega_{2(t,k)}(S_3(0) - S_0(0)) + \xi_{2(t,k)}(S_0(t)) \quad (6)$$

The position/posture estimating portion 82 for $S_2$ and $S_3$, as will be described later, evaluates the reliability about the hypotheses $\{k=1, 2, \ldots, K\}$ for the joint positions $S_{2(t, k)}$ and $S_{3(t, k)}$ of the shoulders at the current time (t). Also, the position/posture estimating portion 82 for $S_2$ and $S_3$, for example, outputs each of the hypotheses $S_{2(t)}$ and $S_{3(t)}$ each having the highest reliability to the position/posture predicting portion 53 for $S_4$ and $S_5$.

The position/posture estimating portion 83 for $S_4$ and $S_5$ receives as its inputs information on the joint positions $S_{4(t-1, k)}$ and $S_{5(t-1, k)}$, of both the elbows at the preceding time (t−1), and information on the estimated positions $S_{2(t)}$ and $S_{3(t)}$ of the joints of the shoulders at the current time (t). Also, the position/posture estimating portion 83 for $S_4$ and $S_5$ calculates the predicted values of the joint positions $S_{4(t, k)}$ and $S_{5(t, k)}$ of both the elbows at the current time (t) by using Expressions (7) and (8):

$$S_4(t,k) = \omega_{4(t,k)}(S_4(0) - S_2(0)) + \xi_{4(t,k)}(S_2(t)) \quad (7)$$

$$S_5(t,k) = \omega_{5(t,k)}(S_5(0) - S_3(0)) + \xi_{5(t,k)}(S_3(t)) \quad (8)$$

The position/posture estimating portion 83 for $S_4$ and $S_5$, as will be described later, evaluates the reliability about the hypotheses $\{k-1, 2, \ldots, K\}$ of the joint positions $S_{4(t, k)}$ and $S_{5(t, k)}$ of both the elbows at the current time (t). Also, the position/posture estimating portion 83 for $S_4$ and $S_5$, for example, outputs each of the hypotheses $S_{4(t)}$ and $S_{5(t)}$ each having the highest reliability to the position/posture predicting portion 54.

The position/posture predicting portion 54 for $S_6$ and $S_7$ receives as its inputs information on the joint positions $S_{6(t-1, k)}$ and $S_{7(t-1, k)}$ of both the arms at the preceding time (t−1), and information on the joint positions $S_{4(t)}$ and $S_{5(t)}$ of both the elbows at the current time (t). Also, the position/posture predicting portion 54 for $S_6$ and $S_7$ calculates the predicted values of the joint positions $S_{6(t, k)}$ and $S_{7(t, k)}$ of both the elbows at the current time (t) by using Expressions (9) and (10):

$$S_6(t,k) = \omega_{6(t,k)}(S_6(0) - S_4(0)) + \xi_{6(t,k)}(S_4(t)) \quad (9)$$

$$S_7(t,k) = \omega_{7(t,k)}(S_7(0) - S_5(0)) + \xi_{7(t,k)}(S_5(t)) \quad (10)$$

The position/posture estimating portion 84 for $S_8$ and $S_7$, as will be described later, evaluates the reliability about the hypotheses {k–1, 2, K} for the joint positions $S_{6(t, k)}$ and $S_{7(t, k)}$ of both the arms at the current time (t). Also, the position/posture estimating portion 84 for $S_6$ and $S_7$, for example, outputs the hypotheses $S_{6(t)}$ and $S_{7(t)}$ each having the highest reliability as the joint positions of both the arms.

In addition, a constitution for predicting the joints of the lower half of the body shown in FIG. 9 includes a position/posture predicting portion 55 for $S_8$, a position/posture estimating portion 85 for $S_8$, a position/posture predicting portion 56 for $S_9$ and $S_{10}$, a position/posture estimating portion 86 for $S_9$ and $S_{10}$, a position/posture predicting portion 57 for $S_{11}$ and $S_{12}$, a position/posture estimating portion 87 for $S_{11}$ and $S_{12}$, a position/posture predicting portion 58 for $S_{13}$ and $S_{14}$, and a position/posture estimating portion 88 for $S_{13}$ and $S_{14}$. Here, the position/posture predicting portion 55 for $S_8$ predicts a position and a posture of the joint $S_8$ of the back. The position/posture predicting portion 56 for $S_9$ and $S_{10}$ predicts positions and postures of the joints $S_9$ and $S_{10}$ of the waist in accordance with the estimation results about the joints $S_8$ of the back. The position/posture predicting portion 57 for $S_{11}$ and $S_{12}$ predicts positions and postures of the joints $S_{11}$ and $S_{12}$ of both the knees in accordance with the estimation results about the joints $S_9$ and $S_{10}$ of the waist. Also, the position/posture predicting portion 53 for $S_{13}$ and $S_{14}$ predicts positions and postures of the joints $S_{13}$ and $S_{14}$ of both the feet in accordance with the estimation results about the joints $S_{11}$ and $S_{12}$ of both the knees.

The position/posture predicting portion 55 for $S_8$ receives as its inputs information on the joint position $S_{8(t-1, k)}$ of the back at the preceding time (t–1), and information on the joint position $S_{0(t)}$ of the neck at the current time (t). Also, the position/posture predicting portion 55 for $S_8$ calculates the predicted value of the joint position $S_{8(t, k)}$ of the back at the current time (t) by using Expression (11):

$$S_8(t,k)=\omega_{8(t,k)}(S_8(0)-S_0(0))+\xi_{8(t,k)}(S_8(t)) \quad (11)$$

The position/posture estimating portion 85 for $S_8$, as will be described later, evaluates the reliability about the hypotheses {k–1, 2, ..., K} for the joint position $S_{8(t, k)}$ of the back at the current time (t). Also, the position/posture estimating portion 85 for $S_8$, for example, outputs the hypothesis $S_{8(t)}$ having the highest reliability to the position/posture predicting portion 56.

The position/posture predicting portion 56 for $S_9$ and $S_{10}$ receives as its inputs information on the joint position $S_{9(t-1, k)}$ of the waist at the preceding time (t–1), and information on the joint position $S_{8(t)}$ of the back at the current time (t). Also, the position/posture predicting portion 56 for $S_9$ and $S_{10}$ calculates the predicted values of the joint positions $S_{9(t, k)}$ and $S_{10(t, k)}$ of the shoulders at the current time (t) by using Expressions (12) and (13):

$$S_9(t,k)=\omega_{9(t,k)}(S_9(0)-S_8(0))+\xi_{9(t,k)}(S_8(t)) \quad (12)$$

$$S_{10}(t,k)=\omega_{10(t,k)}(S_{10}(0)-S_8(0))+\xi_{10(t,k)}(S_8(t)) \quad (13)$$

The position/posture estimating portion 86 for $S_9$ and $S_{10}$, as will be described later, evaluates the reliability about the hypotheses {k=1, 2, K} for the joint positions $S_{9(t, k)}$ and $S_{10(t, k)}$ of the waist at the current time (t). Also, the position/posture estimating portion 86 for $S_9$ and $S_{10}$, for example, outputs each of the hypothesizes $S_{9(t)}$ and $S_{10(t)}$ each having the highest reliability to the position/posture predicting portion 57.

The position/posture predicting portion 57 for $S_{11}$ and $S_{12}$ receives as its inputs information on the joint positions $S_{11(t, k)}$ and $S_{12(t, k)}$ of both the knees at the preceding time (t–1), and information on the joint positions $S_{9(t)}$ and $S_{10(t)}$ of the waist at the current time (t). Also, the position/posture predicting portion 57 for $S_{11}$ and $S_{12}$ calculates the predicted values of the joint positions $S_{11(t, k)}$ and $S_{12(t, k)}$ of both, the knees by using Expressions (14) and (15):

$$S_{11}(t,k)=\omega_{11(t,k)}(S_{11}(0)-S_9(0))+\xi_{11(t,k)}(S_9(t)) \quad (14)$$

$$S_{12}(t,k)=\omega_{12(t,k)}(S_{12}(0)-S_{10}(0))+\xi_{12(t,k)}(S_{10}(t)) \quad (15)$$

The position/posture estimating portion 87 for $S_4$ and $S_5$, as will be described later, evaluates the reliability about the hypotheses {k–1, 2, ... K} for the joint positions $S_{11(t, k)}$ and $S_{12(t, k)}$ of both the knees at the current time (t). Also, the position/posture estimating portion 87 for $S_4$ and $S_5$, for example, outputs each of the hypotheses $S_{11(t)}$ and $S_{12(t)}$ each having the highest reliability to the position/posture predicting portion 58.

The position/posture predicting portion 58 for $S_{13}$ and $S_{14}$ receives as its inputs information on the joint-positions $S_{13(t-1, k)}$ and $S_{14(t-1, k)}$ so of both the feet at the preceding time(t–1), and information on the joint positions $S_{11(t)}$ and $S_{12(t)}$ of both the knees at the current time (t). Also, the position/posture predicting portion 58 for $S_{13}$ and $S_{14}$ calculates the predicted values of the joint positions $S_{13(t, k)}$ and $S_{14(t, k)}$ of both the feet at the current time it) by using Expressions (16) and (17);

$$S_{13}(t,k)=\omega_{13(t,k)}(S_{13}(0)-S_{11}(0))+\xi_{13(t,k)}(S_{11}(t)) \quad (16)$$

$$S_{14}(t,k)=\omega_{14(t,k)}(S_{14}(0)-S_{12}(0))+\xi_{14(t,k)}(S_{12}(t)) \quad (17)$$

The position/posture estimating portion 88 for $S_{13}$ and $S_{14}$ evaluates the reliability about the hypotheses {k=1, 2, ..., K} for the joint positions $S_{13(t, k)}$ and $S_{14(t, k)}$ of both the feet at the current time (t). Also, the position/posture estimating portion 88 for $S_{13}$ and $S_{14}$, for example, outputs each of the hypotheses $S_{13(t)}$ and $S_{14(t)}$ each having the highest reliability as the joint positions of both the feet.

The adjacent joint points are predicted in accordance with the tracking precision (probability) in such a manner, which results in that the motion of the whole body can be predicted with the less hypotheses. For example, when the number of hypotheses for the joint points (the number of prediction filters) is set as 10, and the number of 15 joints are simultaneously predicted, the $10^{15}$ hypotheses are necessary. However, when the adjacent joint points are hierarchically predicted, the 150 (=10×15) hypotheses have only to be set.

In addition, with this technique, the reliability of the tracking results about the preceding joint point $S_{k-1}$ is evaluated, and the prediction model (parameters) of the current joint point $S_k$ are dynamically changed. As a result, for example, when the estimation results about the joint $S_0$ of the neck is not satisfactory, it is possible to prevent such reduction in tracking precision due to the accommodated error in the hierarchies as to exert an influence on ail the joint points. For example, in the case where the reliability of the tracking results about the joint point $S_4$ has the low evaluation value, when the motion of the joint point $S_6$ is predicted and tracked, a predicted position (x, y, z) having the joint point $S_4$ as a center is regarded as a rotational center of the arm ($S_4$-$S_6$) and the motion of the joint point $S_6$ is predicted and tracked while the predicted position (x, y, z) having the joint point $S_4$ as the center is probabilistically changed. Finally, the motion of the arm ($S_{4'}$-$S_6$) is estimated, thereby making it possible to estimate a new joint point $S_{4'}$ of the knee. In this example, the estimation results about the arm ($S_{4'}$-$S_6$) can be obtained as the proper joint position of the elbow. Hence, the estimation results about the joint point. $S_{4'}$ of the elbow can also be fed back to the estimation results about the upper arm ($S_2$-$S_4$).

FIGS. 11A to 11C are respectively schematic views explaining processing in the posture/position projecting portion 6, processing in the reliability evaluating portion 7, and processing in the posture/position estimating portion 8.

The posture/position projecting portion 6 projects a predicted position $(x, y, z)_k$ obtained based on the hypotheses k for the joints on a two-dimensional image $(u, v, depth)_k$ plane. That is to say, the posture/position projecting portion 6 projects the hypotheses predicted in the position/posture predicting portions 51 to 58 shown in FIGS. 8 and 9 on the two-dimensional image plane in accordance with a projection matrix obtained through the camera calibration. With regard to a concrete example, for example, the coordinate values of the predicted position (x, y, z) obtained based on the hypotheses for the joint $S_7$ of the right arm shown in FIG. 11A are projected on an observation image plane as shown in FIG. HE, thereby obtaining the projected position and parallax, (u, v, depth) on the two-dimensional image plane.

The reliability evaluating portion 7 evaluates the similarity between the image information on the projection position on the observation image plane obtained based on the hypotheses, and the previously preserved image information on the model image. Also, the reliability evaluating portion 7 calculates the reliability (probability) about the predicted hypotheses. Here, the image information (such the image texture, the color distribution, and the parallax within a certain window) which is preserved in the phase of initialization can be used as the image information on the model image. In addition, for example, the normal correlation using these image patterns, or the matching about the color distribution characteristics among these image patterns can be used in a similarity evaluating method.

The matching evaluation is performed as follows. That is to say, when the three-dimensional position obtained based on the hypotheses for the joint points $S_{m(t, k)}$ (m: a joint point number, k: a number of hypothesis) at the current time (t) and predicted by the means for hierarchically predicting a motion is projected on the two-dimensional image plane at the current time (t), the three-dimensional region position corresponding to the image region obtained in the phase of the initialization is subjected to processing for a rotation (R) and a transfer (T) by using motion prediction parameters (R, T) of the hypothesis. As a result, the two-dimensional model image pattern is obtained. Also, the similarity between the resulting two-dimensional model image pattern and the image pattern of the projected position based on the hypothesis is evaluated, and a matching score is calculated.

The posture/position estimating portion 8 estimates the positions and postures of the joints $S_m$ obtained based on the similarity evaluation value (probability). That is to say, the posture/position estimating portion 8 determines the positions and postures of the joints by executing statistical processing for an average state having the probability in the predicted positions based on the hypotheses as the degree of a contribution. More specifically, for example, as shown in FIG. 11B, the projected portion on the two-dimensional image plane obtained based on the hypotheses for the joint $S_7$ of the right arm is statistically processed in accordance with the reliability (probability) evaluated through the matching processing in the reliability evaluating portion 7. As a result, as shown in FIG. 11C, the position of the joint $S_7$ of the right arm is estimated.

As described above, the joint position at the current time is hierarchically predicted by using the kinematics model of the objective person, which results in that the positions and postures in the three-dimensional space of the objective person in the general environment can be robustly estimated. In addition, by using the two or more cameras, the kinematics model of the objective person can be readily generated, and also it is possible to improve the estimation precisian for the positions and postures of the objective person. In addition, this technique is robust against the environmental change because it uses neither of a background difference and a time difference. Also, the position, posture and motion of the objective person can be tracked without using any of the markers. Consequently, the natural HMI can be realized without imposing a burden on the objective person.

It should be understood by those skilled in the art that various modifications, combinations, sub-combinations and alterations may occur depending on design requirements and other factors insofar as they are within the scope of the appended claims or the equivalents thereof.

What is claimed is:

1. A motion capture apparatus for tracking three-dimensional positions and postures of joints, and limbs of an objective person, said motion capture apparatus comprising:
    generating means for generating a kinematics model having joints connected to one another from an observation image of said objective person;
    predicting means for hierarchically calculating predicted positions at a current time of the joints of said objective person in accordance with a constraint of coupling among the joints and predicted positions at a preceding time of the joints in said kinematics model, and predicting three-dimensional positions and pastures of the joints and said limbs of said objective person at the current time;
    projecting means for projecting the three-dimensional positions and postures of the joints and the limbs of objective person at the current time on a two-dimensional image plane, the three-dimensional positions and postures being predicted by said predicting means;
    evaluating means for evaluating reliability about projection positions projected by said projecting means in accordance with the observation image of said objective person; and
    estimating means for estimating the three-dimensional positions and postures of the joints and the limbs of objective person at said current time in accordance with an evaluation result about said reliability.

2. The motion capture apparatus according to claim 1, further comprising:
    distance image generating means for generating a distance image from said observation image;
    face detecting means for detecting a position and a distance to a face region from said observation image;
    mask generating means for generating a mash image with said objective person as a foreground in accordance with said distance image and the distance to the face;
    color distribution calculating means for calculating a color histogram about said face region;
    hand detection window generating means for generating hand detection windows in predetermined positions, respectively, in accordance with the position and the distance to said face region;
    hand detecting means for detecting positions and distances to respective hands in accordance with the color histogram about said face region, the positions of said hand detection windows, and said mask image; and
    joint position calculating means for calculating positions of the joints of said kinematics model in accordance with the position and the distance to said face, and the positions and the distances to said respective hands.

3. The motion capture apparatus according to claim 2, wherein said joint position calculating means sets media on a Y axis of the joints of elbows in a foreground region of said mask image as Y coordinates of the joints of the elbows, obtains an approximate straight line for upper arm portions in a state in which media on the Y axis of the upper arm portions in the foreground region of said mask image are set as Y coordinates of the upper arms, and calculates intersections between an X axis and joints of shoulders, and intersections between said approximate straight line and the joints of the shoulders as positions of the joints of the shoulders.

4. The motion capture apparatus according to claim 1, wherein said generating means estimates a parallax image of objective person from said observation image, and inversely projects the parallax image on a three-dimensional space to calculate three-dimensional positions and postures of the joints and the limbs of said objective person, generating kinematics model.

5. The motion capture apparatus according to claim 1, wherein said projecting means projects the three-dimensional positions and the postures of the joints and the limbs at the current time predicted by said predicting means by obtaining projection positions on the two-dimensional image corresponding to the positions in the three-dimensional space in accordance with a projection matrix obtained through camera calibration.

6. The motion capture apparatus according to claim 1, wherein said evaluating means calculates a similarity between image information on the observation image corresponding to said projection positions, and previously preserved image information on the joints and the limbs, thereby evaluating said reliability.

7. The motion capture apparatus according to claim 1, wherein said estimating means estimates the three-dimensional positions and the postures of the joints and the limbs of objective person at said current time in accordance with an evaluation value for the projection positions projected by said projecting means.

8. The motion capture apparatus according to claim 1, further comprising image observing means including at least, two or more cameras disposed so as to photograph the same objective person, and previously having a positional relationship among said at least two or more cameras, and camera parameters.

9. A motion capture method of tracking three-dimensional positions and postures of joints and limbs of an objective person, said motion capture method comprising the steps of:
  generating a kinematics model having joints connected to one another from an observation image of said objective person;
  hierarchically calculating predicted positions at a current time of the joints of said objective person in accordance with a constraint of coupling among the joints and predicted positions at a preceding time of the joints in said kinematics model, and predicting three-dimensional positions and postures of the joints and the limbs of said objective person at the current time;
  projecting the three-dimensional positions and postures of the joints and the limbs of objective person at the current time on a two-dimensional image plane, the three-dimensional, positions and postures being predicted, in said predicting step;
  evaluating reliability about projection positions projected in said projecting step in accordance with the observation image ox said objective person; and
  estimating the three-dimensional positions and postures of the joints and the limbs of said objective person at said current time in accordance with an evaluation result about said reliability.

10. A non-transitory computer-readable medium storing a motion capture program for executing processing for tracking three-dimensional positions and postures of joints and limbs of an objective person, said motion capture program comprising the steps of:
  generating a kinematics model having joints connected to one another from an observation image of said objective person;
  hierarchically calculating predicted positions at a current time of the joints of said objective person in accordance with a constraint of coupling among the joints and predicted positions at a preceding time of the joints in said kinematics model, and predicting three-dimensional positions and postures of the joints and the limbs of said objective person at the current time;
  projecting the three-dimensional positions and postures of the joints and the limbs of objective person at the current time on a two-dimensional image plane, the three-dimensional positions and postures being predicted in said predicting step;
  evaluating reliability about projection positions projected in said projecting step in accordance with the observation image of said objective person; and
  estimating the three-dimensional positions and postures of the joints and the limbs of said objective person at said current time in accordance with an evaluation result about said reliability.

11. A motion capture apparatus for tracking three-dimensional positions and postures of joints, and limbs of an objective person, said motion capture apparatus comprising:
  a generating portion configured to generate a kinematics model having joints connected to one another from art observation image of said objective person;
  a predicting portion configured to hierarchically calculate predicted positions at a current time of the joints of said objective person in accordance with a constraint of coupling among the joints and predicted positions at a preceding time of the joints in said kinematics model, and predict three-dimensional positions and postures of the joints and said limbs of said objective person at the current time;
  a projecting portion configured to project the three-dimensional positions and postures of the joints and the limbs of objective person at the current time on a two-dimensional, image plane, the three-dimensional positions and postures being predicted by said predicting portion;
  an evaluating portion configured to evaluate reliability about projection positions projected by said projecting portion in accordance with the observation image of said objective person; and
  an estimating portion configured to estimate the three-dimensional positions and postures of the joints and the limbs of objective person at said current time in accordance with an evaluation result about said reliability.

* * * * *